(12) United States Patent
Cao

(10) Patent No.: US 8,101,203 B2
(45) Date of Patent: *Jan. 24, 2012

(54) HARD CAPSULE COMPOSITION AND METHOD OF USE

(76) Inventor: Karl Wei Cao, Richmond (CA)

( * ) Notice: Subject to any disclaimer, the term of this patent is extended or adjusted under 35 U.S.C. 154(b) by 227 days.

This patent is subject to a terminal disclaimer.

(21) Appl. No.: 12/687,285

(22) Filed: Jan. 14, 2010

(65) Prior Publication Data

US 2011/0171298 A1 Jul. 14, 2011

(51) Int. Cl.
*A61K 9/48* (2006.01)
(52) U.S. Cl. ......................... 424/451; 424/453
(58) Field of Classification Search .................. None
See application file for complete search history.

(56) References Cited

U.S. PATENT DOCUMENTS

| | | | |
|---|---|---|---|
| 6,214,376 B1 * | 4/2001 | Gennadios | 424/451 |
| 6,331,205 B1 | 12/2001 | Paris et al. | |
| 6,517,865 B2 | 2/2003 | Cade et al. | |
| 6,635,275 B1 | 10/2003 | Scott et al. | |
| 6,635,279 B2 | 10/2003 | Kolter et al. | |
| 6,783,770 B2 | 8/2004 | Angel et al. | |
| 6,887,307 B1 | 5/2005 | Scott et al. | |
| 6,949,256 B2 * | 9/2005 | Fonkwe et al. | 424/451 |
| 7,041,315 B2 | 5/2006 | Scott et al. | |
| 7,267,718 B2 | 9/2007 | Scott et al. | |
| 2001/0024678 A1 | 9/2001 | Scott et al. | |
| 2004/0091557 A1 | 5/2004 | Hamann | |
| 2006/0165775 A1 * | 7/2006 | Korshak et al. | 424/451 |

OTHER PUBLICATIONS

Nishi K; Osada T, Derwent 2005-377484.

* cited by examiner

*Primary Examiner* — Susan Tran
(74) *Attorney, Agent, or Firm* — Buskop Law Group,PC; Wendy Buskop

(57) ABSTRACT

A method for making a clear hard vegetarian gelatin free two piece capsule by creating a first phase network system using a seaweed extract, a galactomannan extract and a rheology modifier. A filler is created for the first phase network by blending a water, a crystalline alcohol, a polysaccharide, and a sugar alcohol at a temperature less than 80 Fahrenheit. The filler is then mixed into the first phase network system forming a biphasic system. Capsules are then formed by dipping conventional moulding pins into the biphasic solution, blowing hot air on the dipped pins in a chamber with a humidity that is no more than 25 percent, blowing away water on the outer surface of the dipped pins to bond and lock moisture to the polysaccharide and removing the capsule pieces from the pins. The two piece capsule has an outer surface which is mechanically and dimensionally stable.

21 Claims, No Drawings

HARD CAPSULE COMPOSITION AND METHOD OF USE

FIELD

The present embodiments generally relate to hard capsules produced in two pieces as empty capsules manufactured solely by using vegetable derivatives.

BACKGROUND

A need exists for a hard capsule made from a gelatin alternative not elicited from animals, specifically bovine due to BSE (bovine spongiform encephalitis) concerns. BSE, or more commonly referred to as Mad Cow Disease, is a fatal disease that affects the central nervous system of bovine and commonly believed to be a potential danger to humans.

A further need exists for a method of producing a clear, hard vegetarian gelatin free two piece hard capsule that has mechanical and dimensional stability and can be used on high speed filing machines.

A need exists for a hard capsule that can be used on high speed filling machines without dimpling and reduce costly downtime, maintenance, and environmental impacts associated with the production of hard capsules.

A further need exists for a hard capsule and a process of making the hard capsule that uses seven completely natural ingredients. The natural ingredients can include water in a biphasic solution system.

A further need exists for a method of making a hard capsule that locks moisture into the hard capsule, and that provides a surprisingly hard capsule relatively low in moisture content after drying and free of animal products.

An additional need exists for a hard capsule that has the ability to be filled with extremely hygroscopic material, without crosslinking The present embodiments meet these needs.

DETAILED DESCRIPTION OF THE EMBODIMENTS

Before explaining the present method in detail, it is to be understood that the method is not limited to the particular embodiments and that it can be practiced or carried out in various ways.

One or more embodiments of described method generally relate to a biphasic system for manufacturing a clear, hard, vegetarian, gelatin free, two piece capsule, using a dipping method. One or more embodiments of the method can provide compositions that do not employ mammalian gelatin and, therefore, overcome the disadvantages associated with animal-derived material.

One or more embodiments of the composition do not contain any gelatin. In one or more embodiments, the composition can include the following seven agents: 1) a polysaccharide, 2) a seaweed extract, 3) a rheology modifier, 4) a sugar alcohol, 5) a crystalline alcohol, 6) a galactomannan extract, and 7) water.

In one or more embodiments of the method, a first phase of a biphasic network system can be created using a seaweed extract, a galactomannan extract and a rheology modifier. Then a second phase or filler can be created for the first phase network by blending water, a crystalline alcohol, a polysaccharide, and a sugar alcohol at a temperature less than 80 degrees Fahrenheit.

After the second phase or filler is created, the filler can be mixed into the first phase network system forming a blend while maintaining a temperature of not more than 80 degrees Fahrenheit.

One or more large diameter moulding pins can be dipped into the blend while the blend is maintained at a temperature of not more than 80 degrees Fahrenheit.

In addition, one or more small diameter moulding pins can be dipped into the blend while the blend is maintained at a temperature of not more then 80 degrees Fahrenheit.

The small diameter pin can have a diameter that is from about 1 percent to about 10 percent less in diameter than the large diameter.

After the moulding pins are dipped into the blend, the moulding pins can be put into a chamber with a humidity that is no more than about 25 percent and the water can be blown away from an outer surface of the dipped pins. The hot air used to blow the water away from the outer surface of the dipped pins can be at a temperature from about 70 degrees Celsius to about 77 degrees Celsius.

Accordingly, the water remaining in the capsule can be bonded or locked to the polysaccharide. This can provide capsule pieces that have an outer surface resistant to humidity and moisture, while maintaining a brilliantly clear, mechanically and dimensionally stable hard capsule resistant to crosslinking and hygroscopic material. The clear hard vegetarian and gelatin free two piece capsule surprisingly inhibits microbial activity by bonding or locking of the water to the polysaccharide of the clear hard vegetarian gelatin free two piece capsule upon drying.

The biphasic system produces a clear hard vegetarian gelatin free two piece capsule wherein a dosage amount is inserted between the first and second capsule pieces, assembling the capsule pieces together with an interference fit forming a dosage capsule that resists cracking, brittleness, and some storage conditions, caused by the hot air blown onto the wet capsule, and bonding the moisture to the polysaccharide until a water activity measures from about 0.10 to about 0.60.

The polysaccharide of the biphasic system for the clear hard vegetarian gelatin free two piece capsule can be alginates, agar gum, gellan, pullulan, starch, tara gum, locust bean gum, glucomannan, monosaccharide gums, or combinations thereof.

The seaweed extract for making a clear hard vegetarian gelatin free two piece capsule can be carrageenan, red seaweed, brown seaweed, funoran algae, red algae, brown algae, green algae, kelp, other marine plants, or combinations thereof.

The rheology modifier for making a clear hard vegetarian gelatin free two piece capsule can be xanthan gum, Arabic gum, karaya gum, or combinations thereof.

The sugar alcohol for making a clear hard vegetarian gelatin free two piece capsule can be glycol, glycerol, erythritol, threitol, arabitol, xylitol, polyol, polyhydric acid, polyalcohol, ribotol, or combinations thereof.

The crystalline alcohol for making a clear hard vegetarian gelatin free two piece capsule can be dextrose, glucose, sorbitol, manitol, fructose, fruit sugar derivative alcohols, or combinations thereof.

The galactomannan extract for making a clear hard vegetarian gelatin free two piece capsule can be mannan, locust bean gum, carob, carob gum, carob bean gum, carboin, guar gum, tragacanth gum, or combinations thereof.

The clear hard vegetarian gelatin free two piece capsule can have polysaccharide at a weight percent from about 10.0 to about 32.0, the seaweed exact at a weight percent from about 0.01 to about 20.0, a rheology modifier at a weight percent from about 0.01 to about 15, the sugar alcohol at a weight percent from about 0.001 to about 10.0, a crystalline alcohol at a weight percent from about 0.001 to about 15.0, the galactomannan extract at a weight percent from about 0.001 to about 15.0, and from about 60.0 weight percent to about 90.0 weight percent of water.

In one or more embodiments, the clear hard vegetarian gelatin free two piece capsule can be a suppository or an oral dosage capsule.

In one or more embodiments, a dosage amount can be stored within the clear hard vegetarian gelatin free two piece capsule. The dosage amount can be a liquid or oil, For example, the dosage amount can be a marine extract, a fish oil, a lipid, a botanical or herbal, a vitamin, a synthetic oil, a vegetable liquid, or combinations thereof.

In one or more embodiments, the dosage amount can be a dry botanical ingredient, or a vitamin supplement.

The dosage amount can also be a pharmaceutical dosage amount that can be dry or liquid. The dosage amount can be aspirin, antihistamine, acetaminophen, an anti-inflammatory, an antibiotic, or combinations thereof. The dosage amount can further be a nutritional dosage amount.

The clear hard vegetarian gelatin free two piece capsule can also have a flavoring additive added to the filler, the first phase network or combinations thereof. The flavorings can include citrus flavoring, mint flavoring, rum flavoring, fruit flavoring, bubblegum flavoring, vanilla flavoring, chocolate flavoring, licorice flavoring, coffee flavoring, or combinations thereof.

The clear hard vegetarian gelatin free two piece capsule can have an edible coloring added to the first phase network, the filler or combinations thereof. The edible coloring can be azoquinophthalone triphenylmethane, xanthene, indigoid dyes, iron oxides, iron hydroxides, titanium dioxides, carbon black, riboflavin, carotenes, anthocyanines, tumeric, cochineal extracts, chlorophyllin, canthaxanthin, caramel, betannin, or combinations thereof.

The clear hard vegetarian gelatin free two piece can have a coating or banding of a second polysaccharide. The first polysaccharide can be the same as the second polysaccharide. In one or more embodiments, the first polysaccharide can be different from the second polysaccharide.

While these embodiments have been described with emphasis on the embodiments, it should be understood that within the scope of the appended claims, the embodiments might be practiced other than as specifically described herein.

What is claimed is:

1. A method for making a clear hard vegetarian gelatin free two piece capsule consisting essentially of:
   a. creating a first phase network system using a seaweed extract, a galactomannan extract, and a rheology modifier;
   b. creating a filler for the first phase network by blending a water, a crystalline alcohol, a polysaccharide, and a sugar alcohol at a temperature less than 80 degrees Fahrenheit;
   c. mixing the filler into the first phase network system forming a biphasic blend;
   d. dipping a first pin with a large diameter into the blend while maintaining the blend a temperature of not more than 80 degrees Fahrenheit;
   e. dipping a second pin with a small diameter into the blend while maintaining the blend at a temperature of not more than 80 degrees Fahrenheit and wherein the second pin small diameter is from 1 percent to 10 percent less in diameter than the large diameter;
   f. blowing hot air on the dipped pins in a chamber with a humidity that is no more than 25 percent locking water molecules to the polysaccharide;
   g. removing a large diameter capsule piece from the first pin and a small diameter capsule piece from the second pin, wherein each capsule piece has an outer surface resistant to humidity and moisture;
   h. inserting a dosage amount between the first and the second capsule pieces; and assembling the capsule pieces together with an interference fit forming a dosage capsule that resists cracking, brittles, and some storage conditions.

2. The method for making a clear hard vegetarian gelatin free two piece capsule of claim 1, wherein the dosage amount is dry or liquid.

3. The method for making a clear hard vegetarian gelatin free two piece capsule of claim 1, wherein the dosage amount is a dry botanical ingredient or a vitamin supplement.

4. The method for making a clear hard vegetarian gelatin free two piece capsule of claim 2, wherein the liquid is a marine extract, a fish oil, a lipid, a botanical or herbal, a vitamin, a vegetable, or combination thereof.

5. The method for making a clear hard vegetarian gelatin free two piece capsule of claim 1, wherein the dosage amount is a pharmaceutical dosage amount.

6. The method for making a clear hard vegetarian gelatin free two piece capsule of claim 5, wherein the pharmaceutical dosage amount is a dosage amount that is a member of the group consisting of: aspirin, antihistamine, acetaminophen, an anti-inflammatory, an antibiotic, and combinations thereof.

7. The method for making a clear hard vegetarian gelatin free two piece capsule of claim 1, wherein the hot air is at a temperature from 70 degrees Celsius to 77 degrees Celsius.

8. The method for making a clear hard vegetarian gelatin free two piece capsule of claim 1, wherein the hot air is blown on the capsule until a water activity measures from 0.10 to 0.6.

9. The method for making a clear hard vegetarian gelatin free two piece capsule of claim 1, wherein the polysaccharide is a member of the group consisting of: alginates, agar gum, gellan, pullulan, starch, tara gum, locust bean gum, glucomannan, monosaccharide gums, and combinations thereof.

10. The method for making a clear hard vegetarian gelatin free two piece capsule of claim 1, wherein the seaweed extract is a member of the group consisting of:
    carrageenan, red seaweed, brown seaweed, funoran algae, red algae, brown algae, green algae, kelp, other marine plants, and combinations thereof.

11. The method for making a clear hard vegetarian gelatin free two piece capsule of claim 1, wherein the rheology modifier is a xanthan gum, arabic gum, and karaya gum, or combinations thereof.

12. The method for making a clear hard vegetarian gelatin free two piece capsule of claim 1, wherein the sugar alcohol is a member of the group consisting of: glycol, glycerol, erythritol, threitol, arabitol, xylitol, polyol, polyhydric acid, polyalcohol, ribotol, and combinations thereof.

13. The method for making a clear hard vegetarian gelatin free two piece capsule of claim 1, wherein the crystalline alcohol is a member of the group consisting of:
    dextrose, glucose, sorbitol, manitol, fructose, fruit sugar derivative alcohols, and combinations thereof.

14. The method for making a clear hard vegetarian gelatin free two piece capsule of claim 1, wherein the galactomannan extract is a member of the group consisting of:

mannan, locust bean gum, carob, carob gum, carob bean gum, carboin, guar gum, tragacanth gum, and combinations thereof.

15. The method for making a clear hard vegetarian gelatin free two piece capsule of claim 1, wherein the capsule is a suppository or an oral dosage capsule.

16. The method for making a clear hard vegetarian gelatin free two piece capsule of claim 1, wherein the dosage amount is a nutritional dosage amount.

17. The method for making a clear hard vegetarian gelatin free two piece capsule of claim 1, further comprising the step of adding a flavoring additive to the filler, the first phase network, or combinations thereof.

18. The method for making a clear hard vegetarian gelatin free two piece capsule of claim 17, wherein the flavoring additive is a member of the group consisting of: citrus flavoring, mint flavoring, rum flavoring, fruit flavoring, bubblegum flavoring, vanilla flavoring, chocolate flavoring, licorice flavoring, coffee flavoring, and combinations thereof.

19. The method for making a clear hard vegetarian gelatin free two piece capsule of claim 1, further comprising the step of adding an edible coloring to the first phase network, the filler, or combinations thereof.

20. The method for making a clear hard vegetarian gelatin free two piece capsule of claim 19, wherein the edible coloring is a member of the group consisting of:
azoquinophthalone triphenylmethane, xanthene, indigoid dyes, iron oxides, iron hydroxides, titanium dioxides, carbon black, riboflavin, carotenes, anthocyanines, tumeric, cochineal extracts, chlorophyllin, canthaxanthin, caramel, betannin, and combinations thereof.

21. A method for making a clear hard vegetarian gelatin free two piece capsule consisting essentially of:

a. creating a first phase network system using a seaweed extract from 0.01 weight percent to 20 weight percent of a biphasic blend, a galactomannan extract from 0.001 weight percent to 15 weight percent of the biphasic blend, and a rheology modifier from 0.01 weight percent to 15 weight percent of the biphasic blend;

b. creating a filler for the first phase network by blending a water, a crystalline alcohol from 0.001 weight percent to 15 weight percent of the biphasic blend, a polysaccharide from 10 weight percent to 32 weight percent of the biphasic blend, a sugar alcohol from 0.001 weight percent to 10 weight percent of the biphasic blend at a temperature less than 80 degrees Fahrenheit;

c. mixing the filler into the first phase network system forming the biphasic blend;

d. dipping a first pin with a large diameter into the biphasic blend while maintaining the blend a temperature of not more than 80 degrees Fahrenheit;

e. dipping a second pin with a small diameter into the biphasic blend while maintaining the biphasic blend at a temperature of not more then 80 degrees Fahrenheit and wherein the second pin small diameter is from 1 percent to 10 percent less in diameter than the large diameter;

f. blowing hot air on the dipped pins in a chamber with a humidity that is no more than 25 percent locking water molecules to the polysaccharide; and g. removing a large diameter capsule piece from the first pin and a small diameter capsule piece from the second pin, wherein each capsule piece has an outer surface resistant to humidity and moisture.

\* \* \* \* \*